United States Patent
Rasmusson

(10) Patent No.: US 12,274,843 B2
(45) Date of Patent: Apr. 15, 2025

(54) MULTIPLE BALLOON VENOUS OCCLUSION CATHETER

(71) Applicant: Gerstner Medical, LLC, Pittsford, NY (US)

(72) Inventor: Timothy Rasmusson, Buffalo, NY (US)

(73) Assignee: Gerstner Medical, LLC, Pittsford, NY (US)

( * ) Notice: Subject to any disclaimer, the term of this patent is extended or adjusted under 35 U.S.C. 154(b) by 1165 days.

(21) Appl. No.: 16/892,755

(22) Filed: Jun. 4, 2020

(65) Prior Publication Data
US 2020/0289800 A1 Sep. 17, 2020

Related U.S. Application Data

(63) Continuation of application No. 14/514,033, filed on Oct. 14, 2014, now Pat. No. 10,702,678.

(60) Provisional application No. 61/905,404, filed on Nov. 18, 2013, provisional application No. 61/890,700, filed on Oct. 14, 2013.

(51) Int. Cl.
*A61M 25/10* (2013.01)
*A61B 17/12* (2006.01)
*A61M 25/00* (2006.01)

(52) U.S. Cl.
CPC ... *A61M 25/1011* (2013.01); *A61B 17/12045* (2013.01); *A61B 17/12109* (2013.01); *A61B 17/12136* (2013.01); *A61B 17/12163* (2013.01); *A61M 25/0026* (2013.01); *A61M 25/10182* (2013.11); *A61M 2025/1052* (2013.01); *A61M 2025/1079* (2013.01)

(58) Field of Classification Search
CPC ...... A61M 2025/1052; A61M 25/1011; A61M 25/10181; A61M 2025/1013; A61B 17/12136; A61B 17/12045; A61B 17/12109
See application file for complete search history.

(56) References Cited

U.S. PATENT DOCUMENTS

| | | | |
|---|---|---|---|
| 4,273,128 A | 6/1981 | Lary | |
| 4,404,971 A * | 9/1983 | LeVeen | A61B 17/12136 604/509 |
| 4,522,205 A * | 6/1985 | Taylor | A61M 29/02 606/49 |
| 5,312,344 A | 5/1994 | Grinfeld et al. | |
| 5,456,694 A | 10/1995 | Marin | |
| 5,458,574 A | 10/1995 | Machold et al. | |
| 5,505,701 A | 4/1996 | Anaya Fernandez de Lomana | |
| 5,697,905 A | 12/1997 | d'Ambrosio | |
| 5,702,417 A | 12/1997 | Hermann | |
| 5,746,709 A | 5/1998 | Rom et al. | |
| 5,765,559 A | 6/1998 | Kim | |
| 5,788,708 A | 8/1998 | Hegde | |
| 5,820,595 A | 10/1998 | Parodi | |
| 5,904,147 A * | 5/1999 | Conlan | A61M 25/0108 604/914 |

(Continued)

FOREIGN PATENT DOCUMENTS

WO WO 2001/019442 3/2001

*Primary Examiner* — Robert A Lynch
*Assistant Examiner* — Christina C Lauer
(74) *Attorney, Agent, or Firm* — Fish & Richardson P.C.

(57) ABSTRACT

A multiple balloon catheter designed to quickly and easily obtain hemostasis during open and minimal access surgery in the event of venous injury.

13 Claims, 3 Drawing Sheets

(56) References Cited

U.S. PATENT DOCUMENTS

| | | |
|---|---|---|
| 5,951,514 A | 9/1999 | Sahota |
| 6,099,542 A | 8/2000 | Cohn et al. |
| 6,123,725 A | 9/2000 | Aboul-Hosn |
| 6,165,196 A | 12/2000 | Stack et al. |
| 6,210,318 B1 | 4/2001 | Lederman |
| 6,210,365 B1 | 4/2001 | Afzal |
| 6,464,664 B1 | 10/2002 | Jonkman et al. |
| 6,565,552 B1 | 5/2003 | Barbut |
| 6,585,689 B1 | 7/2003 | Macoviak et al. |
| 6,595,953 B1 | 7/2003 | Coppi et al. |
| 6,626,859 B2 | 9/2003 | von Segesser |
| 6,673,040 B1 | 1/2004 | Samson et al. |
| 6,679,871 B2 | 1/2004 | Hahnen |
| 6,685,672 B1 * | 2/2004 | Forman ............... A61M 25/1011 604/101.03 |
| 6,695,810 B2 | 2/2004 | Peacock, III et al. |
| 6,719,724 B1 | 4/2004 | Walker et al. |
| 6,719,781 B1 | 4/2004 | Kim |
| 7,004,926 B2 | 2/2006 | Navia et al. |
| 7,063,679 B2 | 6/2006 | Maguire et al. |
| 7,335,192 B2 | 2/2008 | Keren et al. |
| 7,722,568 B2 | 5/2010 | Lenker et al. |
| 7,780,692 B2 | 8/2010 | Nance et al. |
| 7,849,861 B2 * | 12/2010 | Ravikumar ........ A61M 25/1011 128/898 |
| 8,382,697 B2 | 2/2013 | Brenneman et al. |
| 2001/0001806 A1 | 5/2001 | Turnlund et al. |
| 2001/0029349 A1 | 10/2001 | Leschinsky |
| 2004/0116897 A1 | 6/2004 | Aboul-Hosn |
| 2005/0107817 A1 | 5/2005 | White et al. |
| 2005/0197668 A1 | 9/2005 | Lim et al. |
| 2005/0283181 A1 | 12/2005 | Ravikumar |
| 2007/0135793 A1 | 6/2007 | Barbut et al. |
| 2009/0182188 A1 | 7/2009 | Marseille et al. |

* cited by examiner

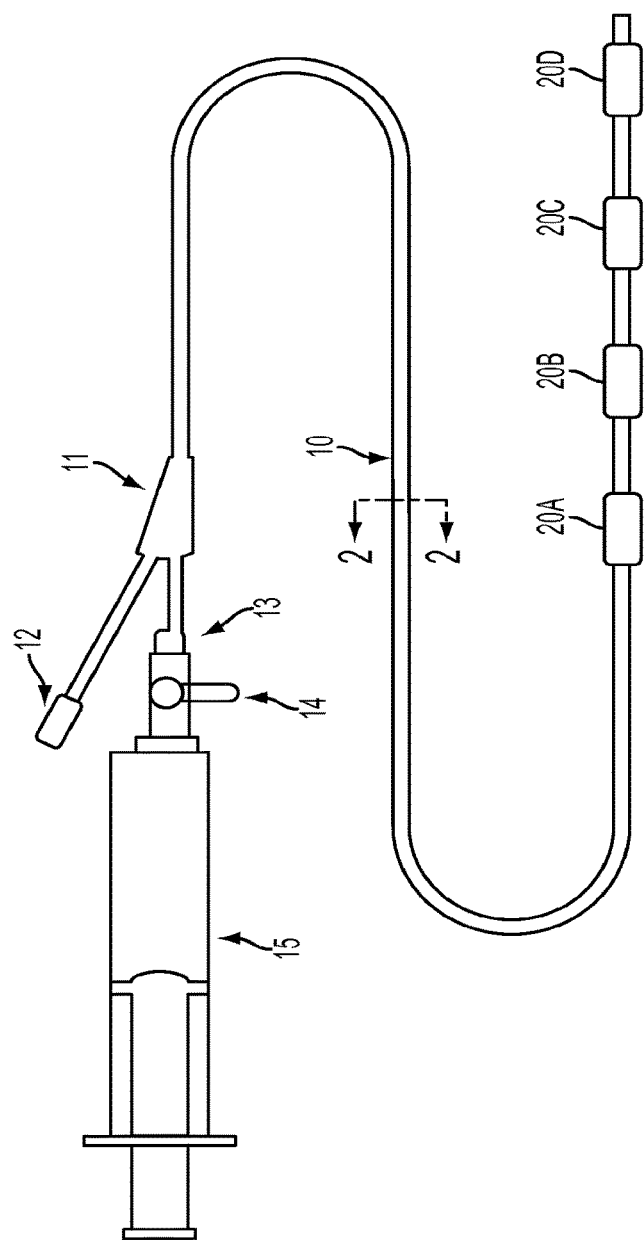
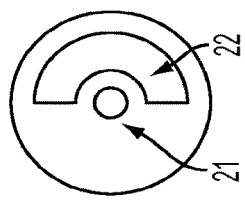
FIG. 1
FIG. 2

MULTIPLE BALLOON VENOUS OCCLUSION CATHETER

This application claims priority to U.S. application Ser. No. 14/514,033, filed on Oct. 14, 2014, which claims priority to U.S. Provisional Application Ser. No. 61/890,700 filed on Oct. 14, 2013 and to U.S. Provisional Application Ser. No. 61/905,404 filed on Nov. 18, 2013 and are incorporated herein by reference.

BACKGROUND OF THE INVENTION

The present invention relates to intravascular devices and methods. More particularly, the invention relates to a multiple balloon catheter which may be placed either during a surgical procedure as needed or preoperatively in one or more venous structures to quickly and safely induce hemostasis in the event of venous injury during a surgical procedure.

All surgical procedures involve some level of risk to the patient. The human body has an extensive arterial and venous vascular structure and system that extends from the heart through the torso to the head and limbs. During surgical procedures, the surgeon must be very careful when working in an area where major arterial and venous structures are located. One risk during surgery is inadvertent damage to the vascular structures in the vicinity of the surgical site which may occur due to surgical instrument slippage or organ/bone manipulation, for example. Particularly in the area of anterior lumbar spinal access and robotic pelvic surgery, the major venous structures may be inadvertently damaged by surgical manipulation. As most present day surgeons will attest, the ability to achieve the required vascular occlusion proximal and distal to the site of injury is often difficult, if not impossible, particularly when utilizing less invasive surgical approaches. The inability to quickly deal with unintentional vascular hemorrhaging during surgery raises the risk of permanent bodily damage or death to the patient. There therefore remains a need for improved devices and methods for obtaining hemostasis in the event of unintended vascular hemorrhaging.

SUMMARY OF THE INVENTION

The present invention addresses the above need by providing a multiple balloon catheter designed to quickly and easily obtain hemostasis during open and minimal access surgery in the event of venous injury. The multiple balloon catheter may be placed either during a surgical procedure as needed or preoperatively in one or more venous structures and thereby allow a surgeon to quickly react to a venous injury by inflating one or more of the balloons (either sequentially or simultaneously) to create hemostasis in a very prompt and efficient manner. The multiple balloons may be serially positioned in the venous structure which allows the surgeon to: 1) occlude proximal and distal blood flow, as well as that from local vascular branches, and 2) selectively occlude particular sections of the venous structure without necessarily knowing the specific location of the venous injury.

DESCRIPTION OF THE DRAWING FIGURES

The above-mentioned and other features and advantages of this invention, and the manner of attaining them, will become apparent and be better understood by reference to the following description of the invention in conjunction with the accompanying drawing, wherein:

FIG. 1 is a simplified side elevational view of one possible embodiment of the inventive catheter;

FIG. 2 is a cross-sectional view as taken through the line 2-2 in FIG. 1;

DETAILED DESCRIPTION OF A PREFERRED EMBODIMENT

Figure 3:
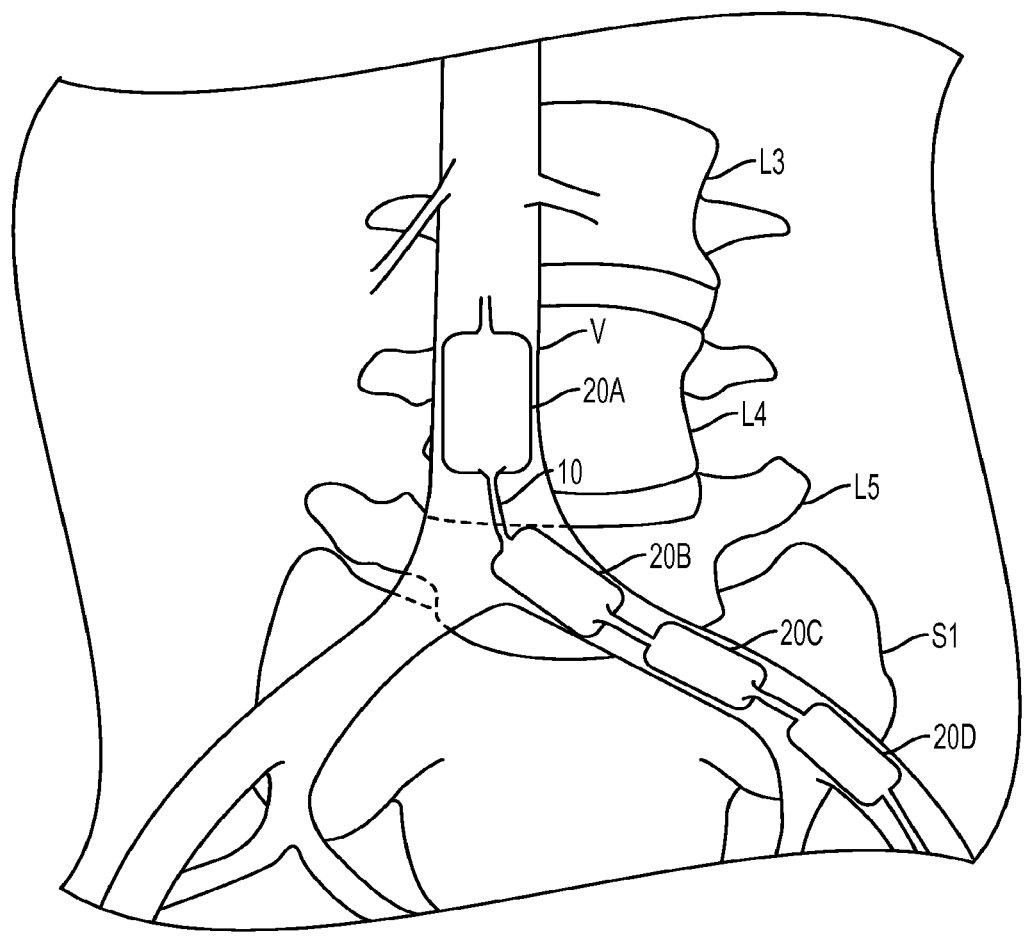
FIG. 3 is a simplified diagrammatic plan view of a typical anterior exposure of a lumbar spine with the catheter of FIG. 1 positioned within the left iliac vein of a patient.

Referring now to FIG. 1, an embodiment of the invention is seen to include a double lumen catheter 10 which may be constructed of any suitable material such as polyurethane or the like, with a central bore 21 extending the length of the catheter 10. Central lumen 21 terminates distally and communicates through a manifold 11 with a luer fitting 12. A second lumen 22 communicates with a luer fitting 13 via manifold 11, and more distally communicates with two or more balloon forming structures 20A-20D which are serially positioned along catheter 10 and are in fluid communication with lumen 22.

The balloon catheter of the present invention is specifically adapted for use in venous systems rather than the currently available balloon catheters used in arterial systems. There are a number of anatomical differences between veins and arteries. Most importantly with regards to the instant invention, arteries are blood vessels which have a generally smaller lumen than veins while also have thicker layers of elastic muscle and connective tissue. The thicker muscles and tissue layers of the artery allow the artery to contract and push blood from the heart to the rest of the body. Veins, on the other hand, do not contract but merely channel blood back to the heart. As such, these veins are generally thin walled vessels which employ a system of valves to prevent back-flow of blood within the vein.

In view of the above, current balloon catheters used in arterial systems are not amenable to use within venous systems. Arterial balloon catheters have higher balloon inflation pressures, on the order of a number of atmospheres (1 atmosphere equals 760 mm Hg (or torr)), which can damage and even burst a vein if overinflated. Balloon forming structures 20A-20D of the present invention are generally thin-walled or highly elastic structures made of low durometer materials requiring much lower inflation pressures (about 5 to about 50 mm Hg, and preferably about 10 to about 30 mm Hg, and most preferably about 15 to about 25 mm Hg) than thicker, less elastic balloons used in arterial balloon catheters. These inflation pressures are generally below venous burst pressure limits (such as that of the iliac vein having a burst pressure greater than about 100 mm Hg) meaning that, even if overinflated, the balloon forming structures 20A-20D would not rupture the vein. However, applying such low pressures to arterial catheter balloons would not cause any inflation of the balloon and therefore no stoppage of blood flow out of the torn or cut vein.

As seen in the surgical example of FIG. 3, catheter 10 is positioned in the left iliac vein, being advanced over a standard guide-wire placed via the left femoral vein. In the event of unintentional venous damage and uncontrolled bleeding, the plunger of the syringe 15 is compressed, forcing fluid or air into lumen 22, inflating the balloons 20A-20D against the wall of the vessel. The volume of this inflation will of course depend on the diameter of the vessel to prevent any further rupturing of the vessel wall. Appropriate means known in the art are included to ensure the balloons cannot overinflate and rupture either the balloon or the surrounding vascular structure. For example, a manometer (not shown) may be provided at the inflow end of the catheter (in one possible embodiment, the balloon inflates to a maximum diameter of 35 mm). Furthermore, the balloons may be made to inflate or deflate either sequentially or simultaneously with optional valves (not shown) positioned on the proximal side of each balloon and which are individually operable to coordinate and control the desired inflation process. The balloons may be of any desired and appropriate shape (e.g., spherical or oblong).

In an embodiment where the balloons are inflated simultaneously, such simultaneous inflation of the balloons prevents, or at least greatly minimizes, migration of the catheter within the vein when the fluid is introduced to the balloons. In this manner, prophylactic placement of catheter to bracket a surgical site ensures that, should a vein tear or rupture, hemostasis may be obtained by inflation of the balloons. It will furthermore be appreciated that, in an embodiment where the balloons are inflated sequentially rather than simultaneously, the balloon closest to the syringe will inflate first 20A, followed sequentially by 20B, 20C and 20D. Thus, for example, should the venous tear be located proximally of balloon 20A (on the side of balloon 20A opposite balloon 20B), inflation of balloons 20B-20D will not be necessary to obtain hemostasis. The provision of multiple balloons (two or more) obviates the need for precise placement of the balloons within the vascular structure since it is more likely at least one of the balloons will be located proximally of a venous tear, wherever that may occur within the surgical site. The provision of multiple balloons strategically placed along a long length of the venous structure is even more compelling when considering the source of the venous tear is not always apparent to the surgeon who would otherwise have to search for the location of the tear prior to applying present day hemostasis techniques and products. As most surgeons of today would attest, it is of the utmost importance to obtain hemostasis as quickly as possible. A hidden venous tear adds time and further uncontrolled bleeding while the surgeon searches for the tear and also creates the potential for further injury as the vascular structure is moved and manipulated during the search and subsequent repair of the tear.

Alternatively, in a further embodiment of the invention of a multi-balloon catheter wherein in balloon is sequentially inflated, the catheter includes multiple lumens wherein one lumen is provided for the guide wire and each respective balloon is inflated or deflated by its own dedicated lumen. With this arrangement, any particular balloon may be inflated/deflated, with such inflation/deflation occurring in any desired order. In this manner, the multi-balloon catheter assists medical personnel in determining the specific location of the venous injury.

Figure 4:
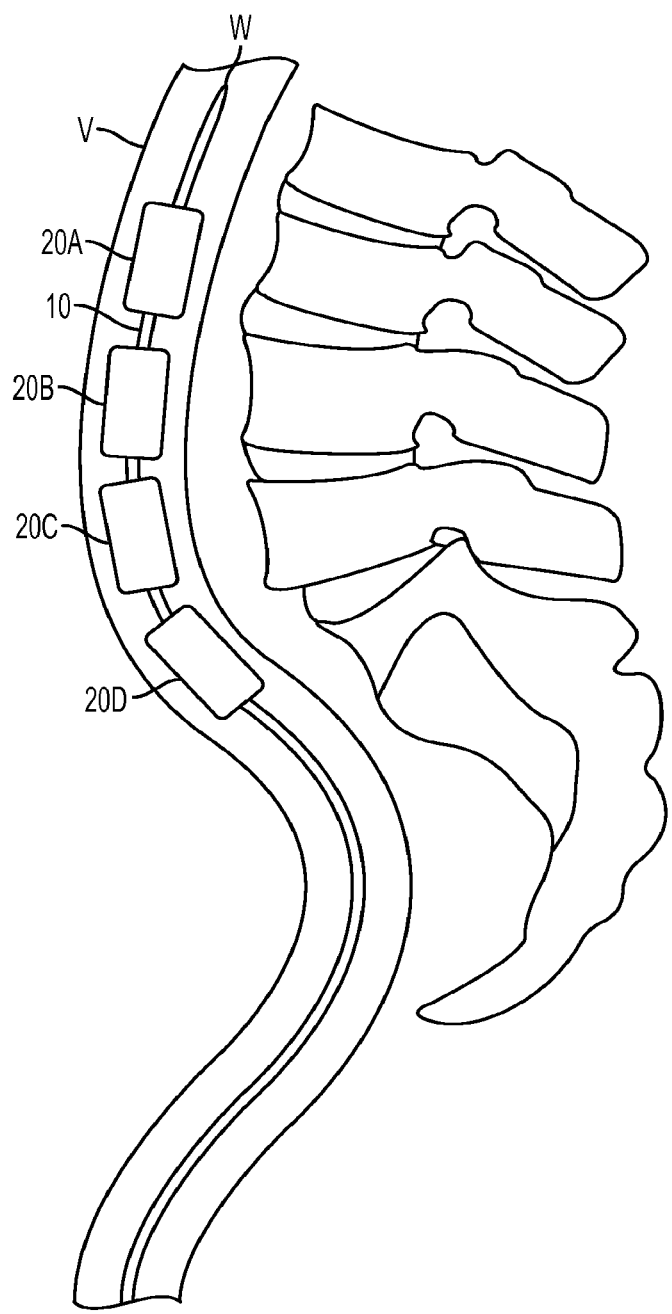
FIG. 4 is a simplified diagrammatic side elevation (lateral) view of FIG. 3.

A clinical example of implementation of the present invention would be during mobilization of the pelvic vessels during an anterior lumbar spinal fusion (see FIGS. 3 and 4). Placed either prophylactically or in the event of injury, catheter 10 could be easily placed with no special training or expertise, the balloons 20A-20D inflated, and bleeding controlled. Repair to the damaged section of the vessel could then be effected either with sutures or one on the many available hemostatic products on the market today.

Another clinical example would be dealing with a venous injury during robotic or laparoscopic pelvic surgery. In this setting there are rarely any options but to convert to an open procedure and attempt to repair the damaged vessel. Catheter 10 could easily be advanced and inflated, stopping the bleeding and allowing repair in a controlled and minimally invasive setting.

As stated above, the catheter 10 (or its guide wire) may be placed prophylactically prior to the main surgery in case it is needed during surgery. It is preferred that catheter 10 have two or more balloons provided in serial fashion with the spacing between the first and last balloons being about the same as or slightly longer than the surgical site such that balloons will be positioned in a place they will be effective if needed and without knowing where a venous rupture may occur. In one possible embodiment, the balloons are positioned approximately 3 to 5 cm apart on center, at the end of the catheter. For example, if the surgical site (where instrumentation is expected to locate during surgery) is 6 inches, the length between the first and last balloons should be about or slightly larger than 6 inches and the first and last balloons placed in the vein adjacent the opposite ends of the surgical site. Thus, should the vein be inadvertently torn somewhere along the surgical site, at least one of the balloons will always be located adjacent to and on the side of the tear from where blood is trying to flow toward the heart so as to stop blood flow through the tear upon balloon inflation. When the balloon is inflated, it will occlude the vein and prevent further blood flow past the balloon. Once the tear is repaired, the balloons are deflated and the catheter removed upon completion of the surgical procedure.

Importantly, the multiple balloon catheter of the present invention stops blood flow from both above and below the situs of venous injury. This is of particular importance when the injury is close to the junction of two major veins and/or wherein there are multiple large venous branches. Simply stopping blood flow from below the injury site will not necessarily stop blood loss as back flow of blood from veins located above the site may still reach the injury site. The multiple balloon catheter of the present invention further closes of the injured vein above the injury site thereby occluded any possible back flow.

It will thus be appreciated that the present invention and method provides a way for a surgeon to react to an unintentional venous tear in an extremely quick and easy fashion not heretofore known or practiced.

While this method and apparatus has been shown and described with reference to certain preferred embodiments thereof, it will be understood by those skilled in the art that various changes in form and details may be made therein without departing from the spirit and scope of the invention as defined in the following claims.

What is claimed is:

1. A method for obtaining hemostasis in a vascular structure, comprising:
   placing a guide wire into a femoral vein of a leg of a patient;
   positioning a catheter having multiple inflatable balloons arranged in a serial fashion along the catheter in an iliac vein of the patient prophylactically prior to a surgical procedure, by advancing the catheter over the guide wire that was placed into the femoral vein while the multiple inflatable balloons are in a deflated state;
   inflating the multiple inflatable balloons to a pressure of about 15-25 mm Hg and a diameter of about 18-35 mm, while the catheter is positioned in the iliac vein of the patient;

repairing venous damage to the iliac vein, while the multiple inflatable balloons remain inflated to the pressure of about 15-25 mm Hg and the diameter of about 18-35 mm;

deflating the multiple inflatable balloons that haves been inflated, after repairing the venous damage to the iliac vein and while the catheter remains positioned in the iliac vein of the patient; and removing the catheter having the multiple inflatable balloons from the iliac vein of the patient after the multiple inflatable balloons have been deflated.

2. The method of claim 1, wherein positioning the catheter having the multiple inflatable balloons in the iliac vein of the patient comprises positioning the catheter so that the multiple inflatable balloons are serially positioned within the iliac vein of the patient.

3. The method of claim 1, wherein positioning the catheter having the multiple inflatable balloons in the iliac vein of the patient comprises placing the catheter having the multiple inflatable balloons in the iliac vein of the patient so that the multiple inflatable balloons bracket a surgical site of the surgical procedure in the patient.

4. The method of claim 1, wherein positioning the catheter having the multiple inflatable balloons in the iliac vein of the patient comprises placing the catheter having the multiple inflatable balloons in the iliac vein so that spacing between a first balloon of the multiple inflatable balloons and a second balloon of the multiple inflatable balloons is about the same as or slightly longer than a surgical site of the surgical procedure in the patient.

5. The method of claim 1, wherein the inflating the multiple inflatable balloons while the catheter is positioned in the iliac vein of the patient is performed responsive to the iliac vein experiencing the venous damage and uncontrolled bleeding.

6. The method of claim 5, wherein:
the venous damage includes a tear or rupture of the iliac vein of the patient; and
the inflating the multiple inflatable balloons includes inflating at least one of the multiple inflatable balloons against a wall of the iliac vein that includes the tear or rupture.

7. The method of claim 5, wherein the inflating the multiple inflatable balloons while the catheter is positioned in the iliac vein of the patient obtains hemostasis in the iliac vein.

8. The method of claim 7, wherein:
the inflating the multiple inflatable balloons while the catheter is positioned in the iliac vein of the patient comprises inflating the multiple inflatable balloons while the catheter is positioned in the iliac vein of the patient, so that a first balloon that is inflated of the multiple inflatable balloons is located above a situs of the venous damage and so that a second balloon that is inflated of the multiple inflated balloons is located below the situs of the venous damage; and obtaining hemostasis in the iliac vein comprises stopping blood flow to the venous damage from both above and below the situs of the venous damage due to the first balloon being inflated at a location above the situs of the venous damage and the second balloon being inflated at a location below the situs of the venous damage.

9. The method of claim 8, wherein the repairing the venous damage to the iliac vein occurs after the multiple inflatable balloons have been inflated to obtain hemostasis in the iliac vein.

10. The method of claim 9,
wherein the removing the catheter having the multiple inflatable balloons from the iliac vein of the patient occurs after the venous damage has been repaired and the surgical procedure completed.

11. The method of claim 1, wherein the inflating the multiple inflatable balloons while the catheter is positioned in the iliac vein of the patient comprises inflating the multiple inflatable balloons below venous burst pressure limits.

12. The method of claim 1, wherein the inflating the multiple inflatable balloons while the catheter is positioned in the iliac vein of the patient comprises simultaneously inflating all of the multiple inflatable balloons.

13. A method for obtaining hemostasis in a vascular structure, comprising:
placing a guide wire into a femoral vein of a leg of a patient;
positioning a catheter having four inflatable balloons arranged in a serial fashion along the catheter in an iliac vein of the patient prophylactically prior to a surgical procedure, by advancing the catheter over the guide wire while the four inflatable balloons are in a deflated state, until the four inflatable balloons are positioned to bracket a surgical site of the surgical procedure;
responsive to the iliac vein of the patient experiencing venous damage and uncontrolled bleeding, inflating the four inflatable balloons to a pressure of 15 to 25 mm Hg and a diameter of 18-35 mm while the catheter is positioned in the iliac vein of the patient, to obtain hemostasis in the venous structure;
repairing the venous damage while the four inflatable balloons remain inflated to the pressure of 15 to 25 mm Hg and the diameter of 18-35 mm, and the four inflatable balloons are positioned in the iliac vein of the patient;
deflating the four inflatable balloons after the venous damage has been repaired, while the catheter is positioned in the iliac vein of the patient; and
removing the catheter having the four inflatable balloons from the iliac vein of the patient after the venous damage has been repaired and the four inflatable balloons have been deflated.

* * * * *